(12) United States Patent
Strong

(10) Patent No.: US 12,274,603 B2
(45) Date of Patent: Apr. 15, 2025

(54) TAMPONS AND METHODS FOR MAKING TAMPONS

(71) Applicant: The Procter & Gamble Company, Cincinnati, OH (US)

(72) Inventor: Kevin Charles Strong, Loveland, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 18/599,355

(22) Filed: Mar. 8, 2024

(65) Prior Publication Data

US 2024/0207104 A1 Jun. 27, 2024

Related U.S. Application Data

(63) Continuation of application No. 16/716,556, filed on Dec. 17, 2019, now Pat. No. 12,186,169.

(60) Provisional application No. 62/834,427, filed on Apr. 16, 2019, provisional application No. 62/780,388, filed on Dec. 17, 2018.

(51) Int. Cl.
*A61F 13/20* (2006.01)
*A61F 13/15* (2006.01)

(52) U.S. Cl.
CPC ...... *A61F 13/2088* (2013.01); *A61F 13/2054* (2013.01); *A61F 13/2068* (2013.01); *A61F 13/208* (2013.01); *A61F 13/15707* (2013.01)

(58) Field of Classification Search
CPC .............. A61F 13/2088; A61F 13/2054; A61F 13/2085; A61F 13/15707; A61F 13/34; A61F 13/2068; A61F 13/208; A61F 13/15699; A61F 13/15747

USPC .................................................. 28/118, 120
See application file for complete search history.

(56) References Cited

U.S. PATENT DOCUMENTS

| | | | |
|---|---|---|---|
| 1,932,383 A | 10/1933 | Richardson | |
| 2,123,750 A | 7/1938 | Schulz | |
| 2,391,343 A * | 12/1945 | Popper | A61F 6/08 604/16 |
| 2,412,391 A | 12/1946 | Crockford | |
| 2,412,861 A * | 12/1946 | Beadle | A61F 13/2051 604/375 |

(Continued)

FOREIGN PATENT DOCUMENTS

| | | |
|---|---|---|
| CN | 1283979 A | 2/2001 |
| CN | 1516569 A | 7/2004 |

(Continued)

OTHER PUBLICATIONS

All Office Actions; U.S. Appl. No. 18/748,285, filed Jun. 20, 2024.

(Continued)

*Primary Examiner* — Amy Vanatta
(74) *Attorney, Agent, or Firm* — Sarah M. DeCristofaro

(57) ABSTRACT

Aspects of the present disclosure relate to methods for making tampons including primary absorbent members and secondary absorbent members. In some configurations, the tampons may be constructed with a primary absorbent member formed by a primary absorbent pad in a rolled configuration. In some configurations, the tampons may be constructed with a primary absorbent member formed by first and second primary absorbent pads positioned in a crossing configuration.

18 Claims, 8 Drawing Sheets

(56) References Cited

U.S. PATENT DOCUMENTS

| | | | |
|---|---|---|---|
| 2,499,414 A * | 3/1950 | Rabell | A61F 13/2068 604/377 |
| 3,397,695 A * | 8/1968 | Voss | A61F 13/2062 604/377 |
| 3,731,687 A * | 5/1973 | Glassman | A61F 13/2068 604/377 |
| 3,732,866 A | 5/1973 | Accavallo | |
| RE27,677 E * | 6/1973 | Glassman | A61F 13/2068 604/286 |
| 3,811,445 A | 5/1974 | Dostal | |
| 4,200,101 A * | 4/1980 | Glassman | A61F 13/2051 604/385.18 |
| 4,318,407 A * | 3/1982 | Woon | A61F 13/2085 28/118 |
| 4,335,720 A * | 6/1982 | Glassman | A61F 13/2051 604/379 |
| 4,624,668 A | 11/1986 | Siegers | |
| 4,835,042 A * | 5/1989 | Dohzono | A61F 13/2051 428/218 |
| 5,891,123 A | 4/1999 | Balzar | |
| 6,186,995 B1 | 2/2001 | Tharpe, Jr. | |
| 6,258,074 B1 | 7/2001 | Prazak | |
| 6,258,075 B1 | 7/2001 | Taylor | |
| 6,840,927 B2 | 1/2005 | Hasse | |
| 7,799,966 B2 * | 9/2010 | Williams | A61F 13/8405 604/360 |
| 8,827,974 B2 * | 9/2014 | Schmidt-Forst | A61F 13/2077 604/385.18 |
| 2001/0021839 A1 | 9/2001 | Kashiwagi | |
| 2003/0097106 A1 | 5/2003 | Hasse et al. | |
| 2003/0097108 A1 | 5/2003 | Hasse et al. | |
| 2003/0097112 A1 | 5/2003 | Gilbert et al. | |
| 2004/0000193 A1 | 1/2004 | Grotendorst | |
| 2004/0019317 A1 | 1/2004 | Takagi | |
| 2005/0055003 A1 | 3/2005 | Bittner et al. | |
| 2005/0096619 A1 | 5/2005 | Costa | |
| 2006/0025742 A1 | 2/2006 | Hasse et al. | |
| 2007/0016156 A1 | 1/2007 | Burgdorf et al. | |
| 2007/0260211 A1 | 11/2007 | Schmidt-forst | |
| 2008/0132868 A1 * | 6/2008 | Jorgensen | A61F 13/2065 604/385.17 |
| 2008/0262463 A1 | 10/2008 | Noel et al. | |
| 2008/0275411 A1 | 11/2008 | Hughes et al. | |
| 2009/0260205 A1 | 10/2009 | Binner et al. | |
| 2010/0069866 A1 | 3/2010 | Binner et al. | |
| 2010/0130953 A1 | 5/2010 | Fung et al. | |
| 2010/0174262 A1 | 7/2010 | Watanabe | |
| 2010/0268182 A1 | 10/2010 | Edgett | |
| 2012/0053550 A1 | 3/2012 | Kinoshita et al. | |
| 2012/0101462 A1 | 4/2012 | Lee | |
| 2012/0277704 A1 | 11/2012 | Marinelli | |
| 2013/0138071 A1 | 5/2013 | Fung et al. | |
| 2013/0160259 A1 | 6/2013 | Mcdaniel et al. | |
| 2015/0157511 A1 | 6/2015 | Strong | |
| 2015/0374558 A1 | 12/2015 | Strong et al. | |
| 2018/0125724 A1 | 5/2018 | Brown et al. | |
| 2020/0188186 A1 | 6/2020 | Strong et al. | |
| 2020/0188189 A1 | 6/2020 | Strong et al. | |
| 2020/0188190 A1 | 6/2020 | Strong | |

FOREIGN PATENT DOCUMENTS

| | | |
|---|---|---|
| CN | 101874756 A | 11/2010 |
| WO | 0061052 A1 | 10/2000 |
| WO | 2000061052 A1 | 10/2000 |
| WO | 02058609 A2 | 8/2002 |
| WO | 02058614 A1 | 8/2002 |
| WO | 03022196 A2 | 3/2003 |
| WO | 2005063161 A1 | 7/2005 |
| WO | 2005112861 A1 | 12/2005 |
| WO | 2007078413 A1 | 7/2007 |
| WO | 2016207242 A1 | 12/2016 |

OTHER PUBLICATIONS

Unpublished U.S. Appl. No. 18/748,285, filed Jun. 20, 2024, Kevin Charles Strong et al.
All Office Actions, U.S. Appl. No. 16/716,556.
All Office Actions, U.S. Appl. No. 16/716,553.
All Office Actions; U.S. Appl. No. 16/716,550, filed Dec. 17, 2019.
All Office Actions; U.S. Appl. No. 18/429,861, filed Feb. 1, 2024.
All Office Actions; U.S. Appl. No. 18/459,475, filed Sep. 1, 2023.
Fiery Software. Delta E, Delta H, Delta T: What Does It Mean ?. Online retrieved from chrome extension://efaidnbmnn-nibpcajpcglclefindmkaj/https://help.fiery.com/fieryxf/KnowledgeBase/ColorManagement/Delta%20E_H_T.pdf, dated 2023, pp. 04.
Gopalakrishnan, "D. Spunbonded Nonwovens"—an Overview, Online retrieved from https://www.fibre2fashion.com/industry-article/1575/spunbonded-nonwovens-an-overview. Year: 2007, pp. 05.
International Search Report and Written Opinion; Application Ser. No. PCT/US2019/066695; dated Mar. 12, 2020, 14 pages.
McLoughlin, J, and Mitchell, A.;"Textiles and Fashion, Materials design and technology", Cambridge: Woodhead Publishing, Retrieved from the Internet: URL:https://www.sciencedirect.com/science/article/pii/B9781845699314000167, Chapter 16, ISBN-978: 0-85709-561-9, Year 2015, pp. 379-411.
Unpublished U.S. Appl. No. 18/429,861, filed Feb. 1, 2024, to Kevin Charles Strong.
Unpublished U.S. Appl. No. 18/459,475, filed Sep. 1, 2023, Kevin Charles Strong et al.
Extended European Search Report and Search Opinion; Application No. 23208447.5; dated Apr. 2, 2024; 08 pages.

* cited by examiner

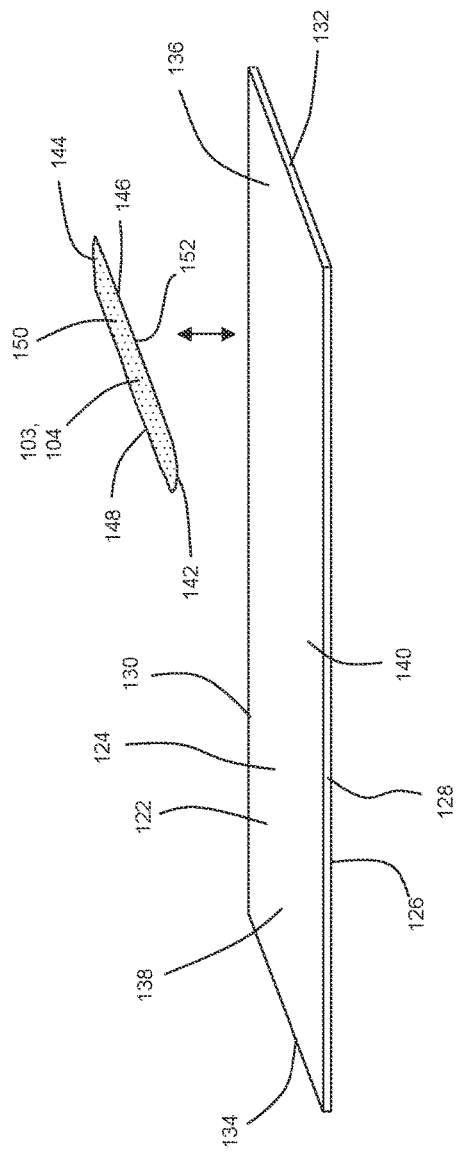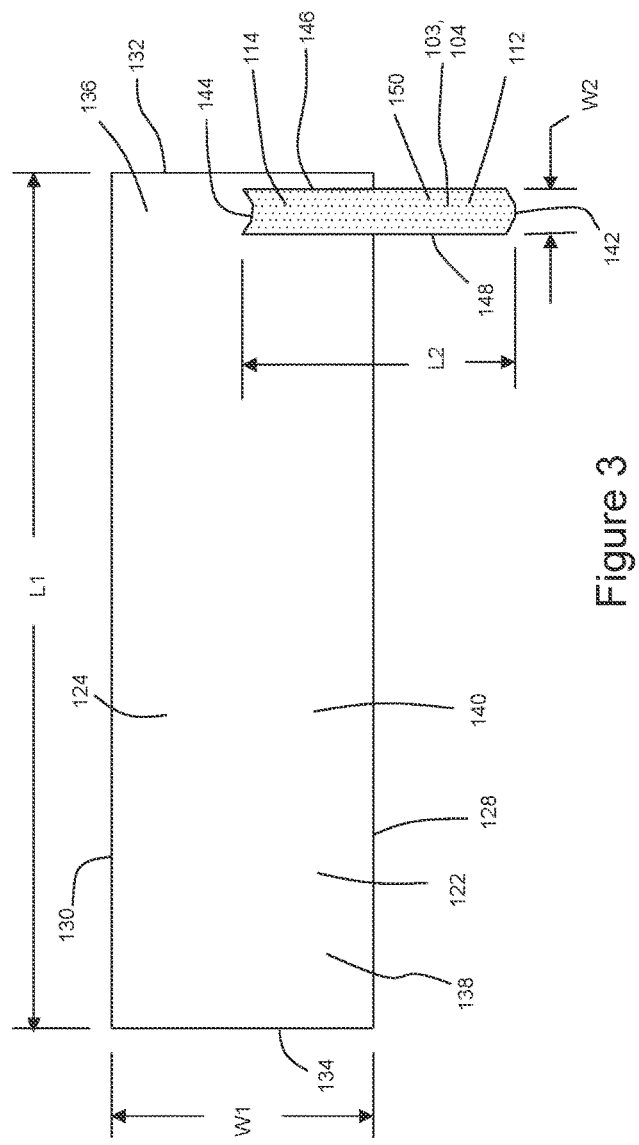

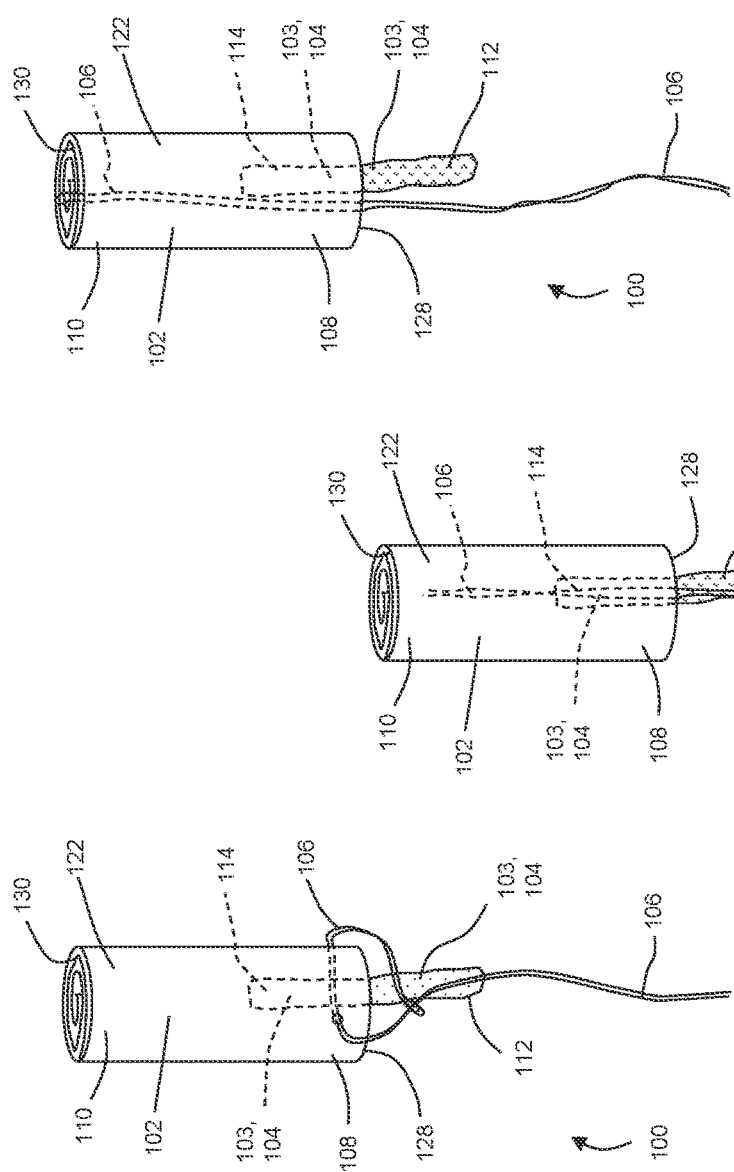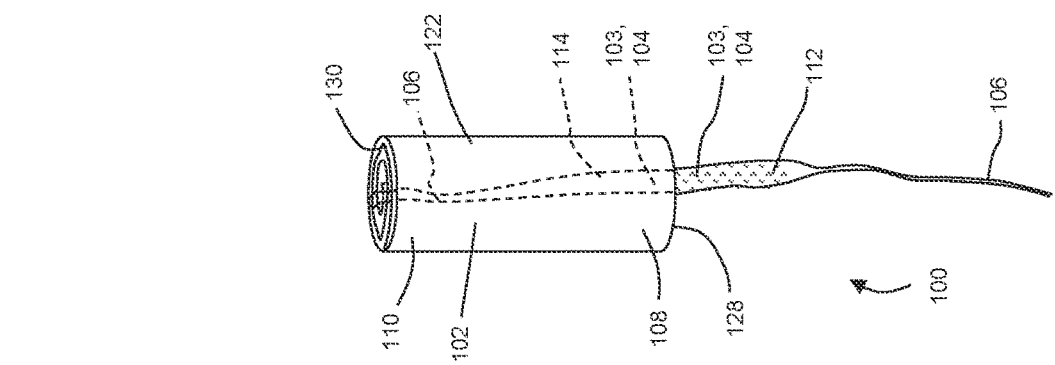

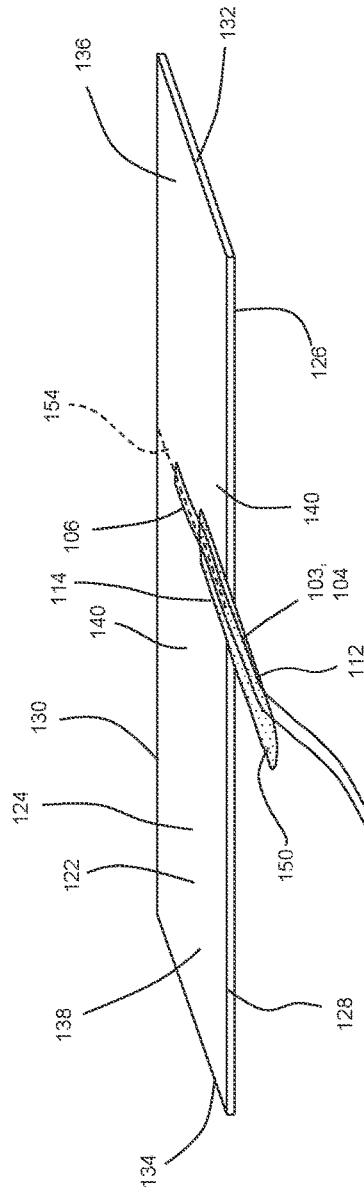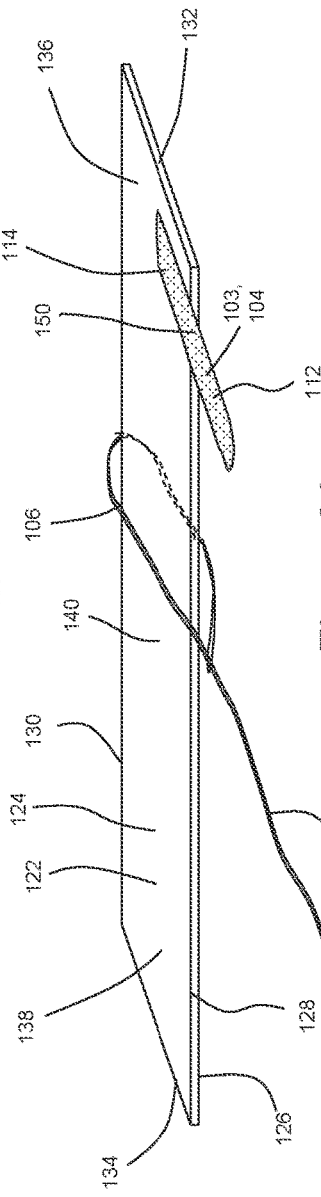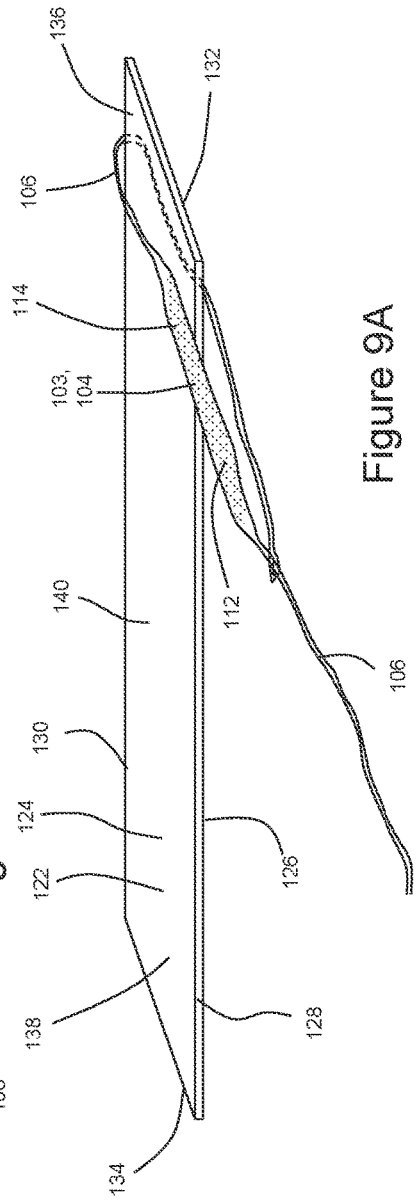
Figure 7A
Figure 8A
Figure 9A

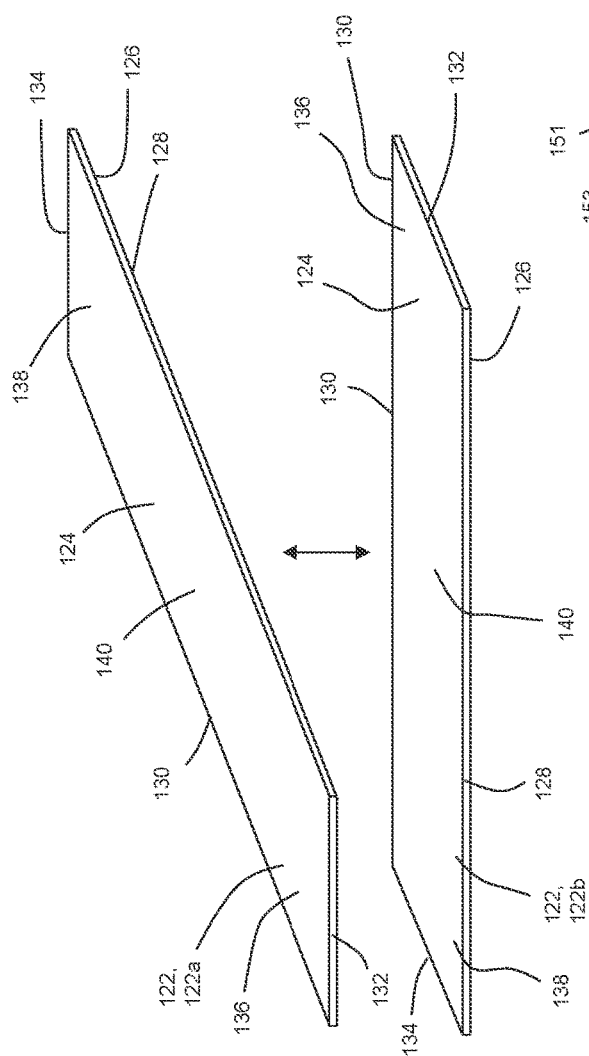
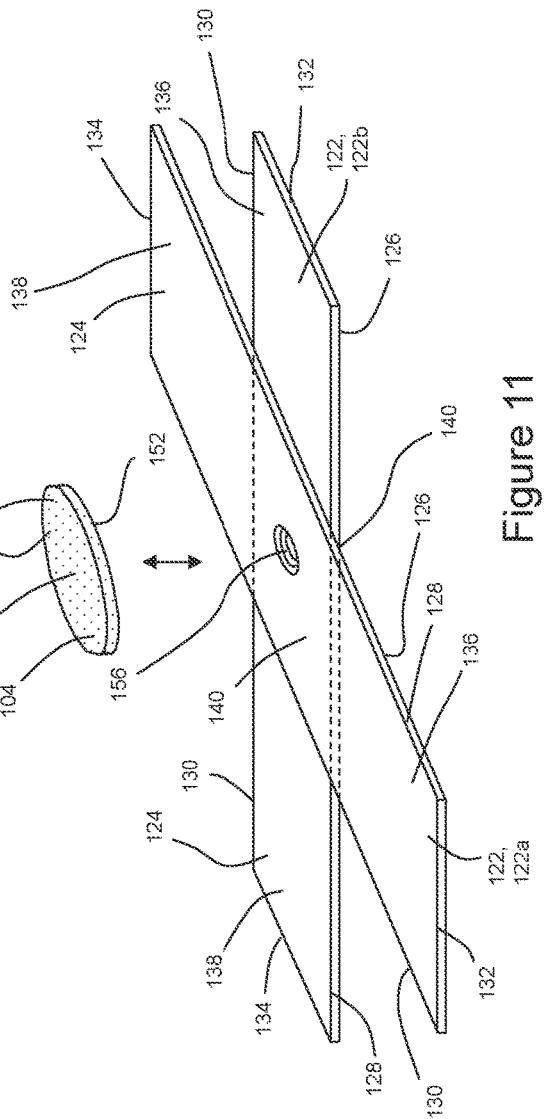

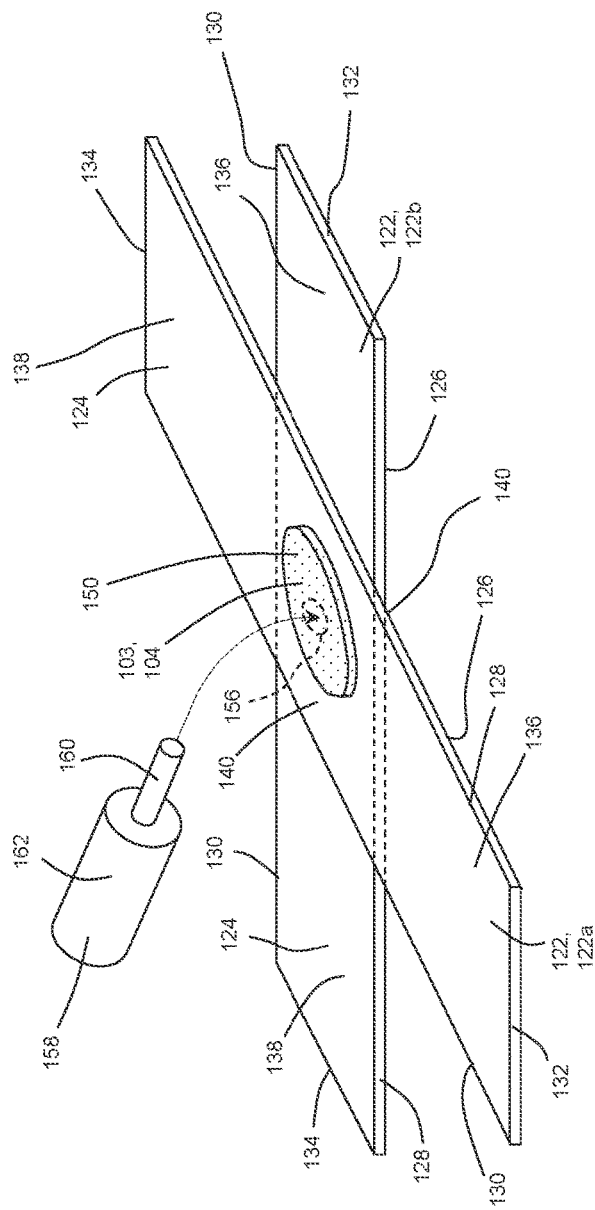
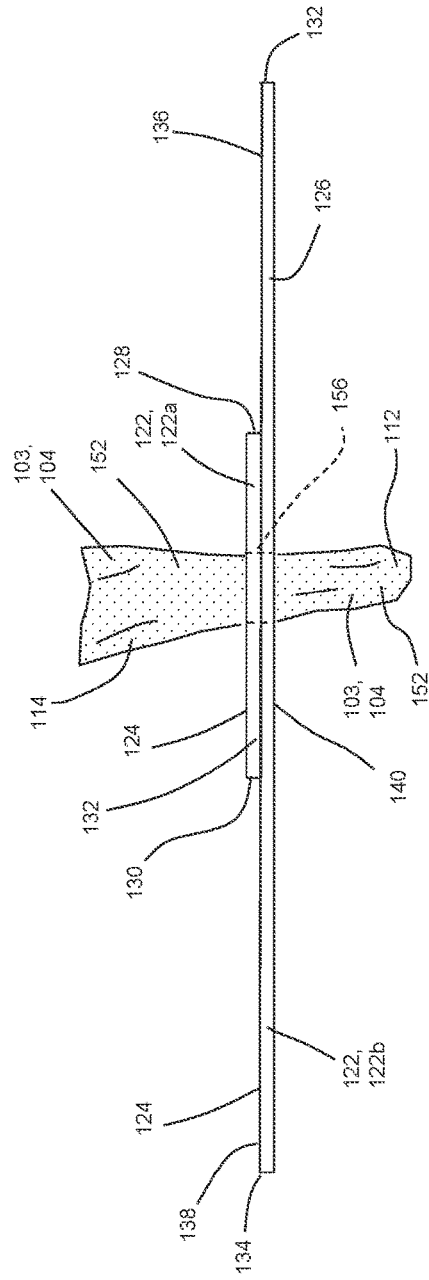

TAMPONS AND METHODS FOR MAKING TAMPONS

CROSS REFERENCE TO RELATED APPLICATION

This application is a continuation of, and claims priority under 35 U.S.C. § 120 to, U.S. patent application Ser. No. 16/716556 filed on Dec. 17, 2019, which claims the benefit, under 35 U.S.C. § 119(e), of U.S. Provisional Patent Application Ser. Nos. 62/834,427 filed on Apr. 16, 2019 and 62/780,388 filed Dec. 17, 2018, the entire disclosures of all of which are fully incorporated by reference herein.

FIELD OF THE INVENTION

The present disclosure relates to tampons and methods for manufacturing tampons, and more particularly, to tampons and methods for making tampons that include primary absorbent members and secondary absorbent members.

BACKGROUND OF THE INVENTION

A wide variety of absorbent catamenial tampons have been known in the art. Some currently commercially available tampons are made from absorbent material configured as an absorbent member which has been compressed into a substantially cylindrical form. Prior to compression, the absorbent member may be rolled, spirally wound, folded, or assembled as a rectangular pad of absorbent material. Conventional catamenial tampons may also be provided with a withdrawal cord connected with the absorbent member. During use, the withdrawal cord may extend out of a user's body following tampon insertion to allow for retrieval and disposal of the used tampon.

In order to provide the desired total absorbency, absorbent members may be formed from batts larger in size than a vaginal orifice. The batts are then compressed to a size with a corresponding increase in rigidity in order to facilitate insertion. As fluid is absorbed, these compressed tampons are configured to re-expand toward an original pre-compressed size, and to eventually become large enough to effectively cover the vaginal cavity and prevent fluid leakage. However, some compressed tampons may not always re-expand sufficiently, or fast enough, to provide a desired coverage against leakage. As such, suppliers of tampons have recognized various mechanisms by which tampons might fail to deliver superior performance. One such mechanism is often referred to in the art as "bypass" failure. Bypass failure occurs when menses travels along the length of the vagina without contacting the tampon, wherein the tampon fails to intercept the flowing menses.

In the past, different approaches have been attempted to address bypass and other forms of tampon failure. For example, some tampons may be constructed with a secondary absorbent material in addition to a compressed primary absorbent material. Advantages of such a secondary absorbent material may include an ability of the tampon to absorb bypass flow in the early stages of wear, as well as an ability of the tampon to absorb residual fluid which may have been "squeezed out" of a prior tampon during removal.

In some configurations, the secondary absorbent material may be made from material such as, for example, fibrous materials formed by a carding process. Various methods and apparatuses may be used to integrate such fibrous secondary absorbent material into assembled tampons. Some manufacturers have utilized the assembly process of withdrawal cords, such as mentioned above, to integrate the secondary absorbent material into the tampon assembly process. For example, in some operations, withdrawal cords may be constructed by advancing one or more strings through a tubular weaver. In turn, manufacturers of tampons with secondary absorbent material have utilized the tubular weaving process to incorporate the secondary absorbent material into the withdrawal cord construction. For example, fleeces of secondary absorbent material may be intermittently combined with the advancing string upstream of the weaver. As such, the string and intermittent lengths of secondary absorbent material advance through the weaver to create a continuous composite yarn wherein the withdrawal cord material and secondary absorbent material are interwoven. Discrete lengths of secondary absorbent material are intermittently formed on the continuous composite yarn. The continuous composite yarn may then be attached to the primary absorbent material during the assembly process with the discrete length of secondary absorbent material connected with the primary absorbent member in a desired location.

However, the above described tampon assembly operations may present various challenges and/or limitations. For example, some tampon manufacturing lines may operate at relatively high speeds. In contrast, the weaving process discussed above may be a relatively slow process with a relatively low throughput. As such, relatively numerous weaving operations may be required to produce sufficient quantities of composite yarn required by the relatively high speed tampon assembly processes. Requiring numerous weaving operations can result in higher costs and complexities for tampon manufacturers. In addition, composite yarn assembly may necessitate intertwining two materials with different properties. For example, in some tampon configurations, the string used to construct the withdrawal cord may be hydrophobic whereas the secondary absorbent material may be hydrophilic. As such, the composite yarn may be assembled such that some portions are constructed with hydrophilic and hydrophobic materials woven together. Such interwoven hydrophilic and hydrophobic materials function in divergent fashions, which in turn, may have a negative effect on the overall performance of the tampon. Further, some withdrawal cords made with a woven construction may be relatively more prone to frayed ends as compared to withdrawal cords constructed differently. Utilizing the above composite yarn assembly process limits the withdrawal cord and/or secondary absorbent material to a woven construction in circumstances wherein it may be preferable to construct the withdrawal cord and/or secondary absorbent material in different ways.

As such, in some instances, it may be desirable to construct the withdrawal cord and the secondary absorbent material as separate parts, as opposed to the integrated construction discussed above. However, further manufacturing challenges and/or limitations can be encountered when utilizing separately constructed withdrawal cords and secondary absorbent material. The introduction of a separately constructed secondary absorbent material into an existing tampon assembly process may require a manufacturer to add new, relatively complex and slow assembly operations, such as stitching, in order to secure the secondary absorbent material to other tampon components.

In some manufacturing processes, primary absorbent members may be constructed by rolling a pad onto itself or placing discrete pads together in a crossing configuration. Depending on the method of construction of the primary absorbent member, it may be desirable to utilize separate components or combinations of integrated components. Consequently, it would be beneficial to provide tampons and methods for producing tampons with secondary absorbent materials and withdrawal cord constructions that can be provided so as to be assembled at relatively high speeds while further providing manufactures with additional flexibilities with respect to material choices and/or construction.

SUMMARY OF THE INVENTION

In one form, a method for making a tampon comprises steps of: providing a first primary absorbent pad comprising a first end region and a second end region separated from the first end region by a central region; providing a second primary absorbent pad comprising a first end region and a second end region separated from the first end region by a central region; overlaying the central region of the first primary absorbent pad on the central region of the second primary absorbent pad in a crossing configuration, wherein the first and second end regions of the first and second primary absorbent pads do not overlap each other; positioning a flexible member on the central region of the first primary absorbent pad; forcing a first portion of the flexible member through the central region of the first primary absorbent pad and the central region of the second primary absorbent pad, wherein the first portion of the flexible member extends outward from the second primary absorbent pad and a second portion of the secondary absorbent member extends outward from the first primary absorbent pad; and compressing the first primary absorbent pad and the second primary absorbent pad into a generally cylindrically shaped primary absorbent member that envelops the second portion of the flexible member.

In another form, a catamenial tampon for use within the vaginal space of a female wearer comprises: a first primary absorbent pad comprising a first end region and a second end region separated from the first end region by a central region; and a second primary absorbent pad comprising a first end region and a second end region separated from the first end region by a central region, wherein the central region of the first primary absorbent pad overlays the central region of the second primary absorbent pad in a crossing configuration such that the first end regions and the second end regions of the first primary absorbent pad and the second primary absorbent pad do not overlap each other; and a flexible member extending through the central regions of the first primary absorbent pad and the second primary absorbent pad, wherein a first portion of the flexible member extends outward from the second primary absorbent pad and wherein a second portion of the flexible member extends outward from the first primary absorbent pad.

In yet another form, a method for making a tampon comprises steps of: providing a primary absorbent pad comprising a first side edge and a second side edge separated from the first side edge to define a width, the primary absorbent pad further comprising a first end edge and a second end edge separated from the first end edge to define a length; positioning a flexible member on the primary absorbent pad, wherein a first portion of the flexible member extends outward from the first side edge of the primary absorbent pad and wherein a second portion of the flexible member extends from the first side edge toward the second side edge of the primary absorbent pad; and rolling the primary absorbent pad into a generally cylindrically shaped primary absorbent member comprising a first end region and an opposing second end region, wherein the first portion of the flexible member extends outward from the first end region of the primary absorbent member and wherein second portion of the flexible member is enveloped by the primary absorbent member.

In still another form, a catamenial tampon for use within the vaginal space of a female wearer comprises: a primary absorbent pad comprising a first side edge and a second side edge separated from the first side edge to define a width, the primary absorbent pad further comprising a first end edge and a second end edge separated from the first end edge to define a length, the primary absorbent pad rolled along the length to define a generally cylindrically shaped primary absorbent member comprising a first end region and an opposing second end region; a flexible member connected with the primary absorbent pad, wherein a first portion of the flexible member extends outward from the first end region of the primary absorbent member and wherein second portion of the flexible member is enveloped by the primary absorbent member; and a withdrawal cord connected with the primary absorbent member.

BRIEF DESCRIPTION OF THE DRAWINGS

FIG. 2 is an illustration of an assembly operation combining a secondary absorbent member and a primary absorbent pad.

FIG. 3 is a top side view of a secondary absorbent member positioned on a primary absorbent pad.

FIG. 6 is an isometric view of a withdrawal cord inserted through a primary absorbent member and a secondary absorbent member, wherein the primary absorbent member is constructed from a primary absorbent pad rolled onto itself.

FIG. 7A is an isometric view of a secondary absorbent member and a withdrawal cord sewn together with a primary absorbent pad.

FIG. 7B is an isometric view of the primary absorbent pad of FIG. 7A rolled onto itself to form a tampon.

FIG. 8A is an isometric view of a withdrawal cord looped around opposing edges of a primary absorbent pad.

FIG. 8B is an isometric view of the primary absorbent pad of FIG. 8A rolled onto itself to form a tampon.

FIG. 9A is an isometric view of an integrally formed withdrawal cord and secondary absorbent member looped around opposing edges of a primary absorbent pad.

FIG. 9B is an isometric view of the primary absorbent pad of FIG. 9A rolled onto itself to form a tampon.

FIG. 10 is an illustration of an assembly operation combining a first primary absorbent pad and second primary absorbent pad in a crossing configuration.

FIG. 11 is an illustration of an assembly operation combining a secondary absorbent member with the first primary absorbent pad and the second primary absorbent pad of FIG. 10.

FIG. 12 is an isometric view of the combined secondary absorbent member, first primary absorbent pad, and second primary absorbent pad of FIG. 11.

FIG. 13 is a front side view of the secondary absorbent member inserted through the first primary absorbent pad and the second primary absorbent pad of FIG. 12.

DETAILED DESCRIPTION OF THE INVENTION

Figure 1:
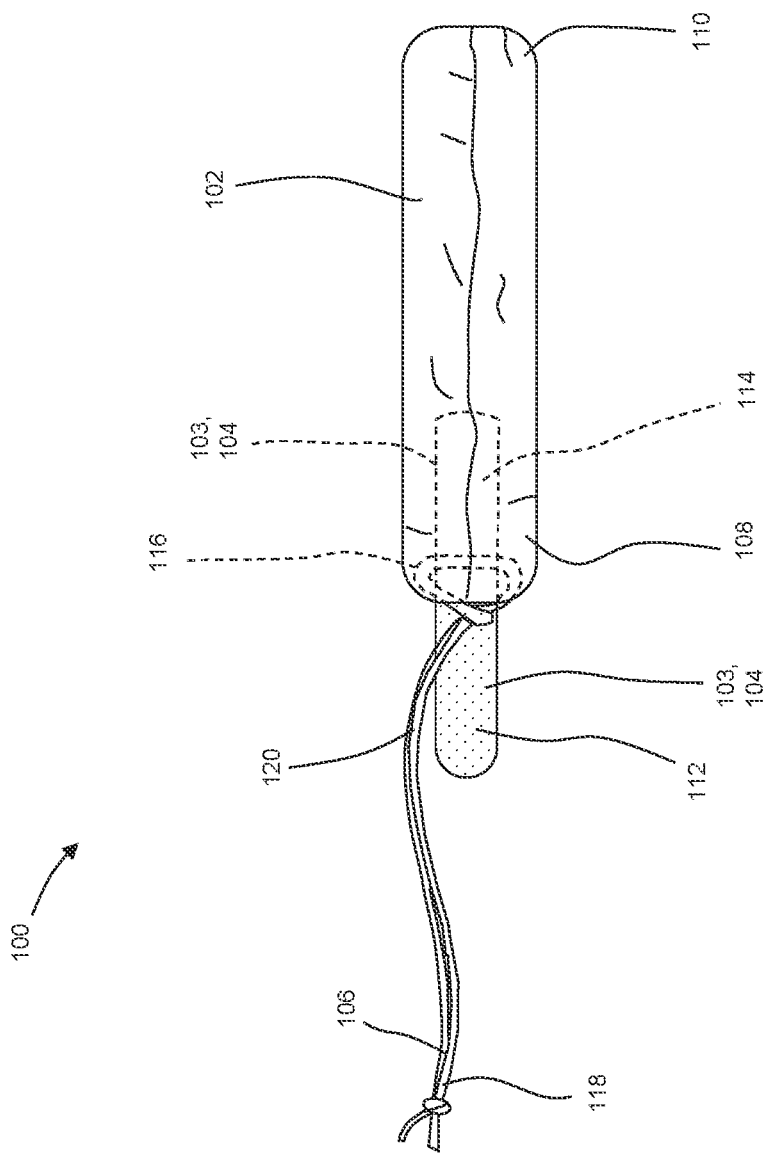
FIG. 1 is a front view of an example catamenial tampon.

The following term explanations may be useful in understanding the present disclosure:

As used herein the term "tampon" refers to any type of absorbent structure which is inserted into the vaginal canal or other body cavities for the absorption of fluid therefrom. Tampons are constructed from an absorbent material that may be compressed into a generally cylindrical configuration in the radial direction, axially along a longitudinal axis or in both the radial and axial directions to provide a tampon which is of a size and stability to allow insertion within the vagina or other body cavity. A tampon which has been so compressed is referred to herein as a "self-sustaining" form. That is, the degree of compression applied to the absorbent material of the tampon pledget is sufficient so that in the subsequent absence of the external forces, the resulting tampon will tend to retain its general shape and size. Tampons have an insertion end, withdrawal end, a length, a width, a longitudinal axis and a radial axis. The tampon's length can be measured from the insertion end to the withdrawal end along the longitudinal axis. In some examples, a compressed tampon for human use may have length within a range from about 30 mm to about 60 mm. A tampon may be straight or non-linear in shape, such as curved along the longitudinal axis. In some examples, a compressed tampon is within a range from about 8 mm to about 20 mm wide. The width of a tampon, unless otherwise stated in the specification, corresponds to the distance across the largest cross-section, along the length of the tampon and perpendicular to the longitudinal axis of the tampon.

The term "stabilized," as used herein, refers to a tampon in a self-sustaining state wherein it has overcome the natural tendency to re-expand to the original size, shape and volume of the absorbent material and overwrap, which comprise the pledget.

As used herein the terms "pledget" or "tampon pledget" are intended to be interchangeable and refer to a construction of absorbent material prior to the compression of such construction into a tampon as described above. Tampon pledgets are sometimes referred to as a tampon blank, or a softwind, and the term "pledget" is intended to include such terms as well.

As used herein the terms "vaginal cavity," "within the vagina" and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity" as used herein.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Aspects of the present disclosure relate to methods for manufacturing tampons, and more particularly, to methods for making tampons including primary absorbent members and secondary absorbent members. In some configurations, the tampons herein may be constructed with a primary absorbent member formed by a primary absorbent pad in a rolled configuration. And in some configurations, the tampons herein may be constructed with a primary absorbent member formed by first and second primary absorbent pads positioned in a crossing configuration.

In a rolled configuration assembly process, a primary absorbent pad may be provided that includes a first side edge and a second side edge separated from each other to define a width, and a first end edge and a second end edge separated from other to define a length. A secondary absorbent member may be positioned on the primary absorbent pad such that a first portion of the secondary absorbent member extends outward from the first side edge of the primary absorbent pad and a second portion of the secondary absorbent member extends from the first side edge toward the second side edge of the primary absorbent pad. The primary absorbent pad is rolled into a generally cylindrically shaped primary absorbent member including a first end region and an opposing second end region, wherein the first portion of the secondary absorbent member extends outward from the first end region of the primary absorbent member and wherein second portion of the secondary absorbent member is enveloped by the primary absorbent member. A withdrawal cord may also be connected with the primary absorbent pad in different ways. For example, in some configurations, the withdrawal cord may loop around the first side edge and the second side edge of the primary absorbent pad. In other examples, the withdrawal cord may be inserted through the primary absorbent pad and the second portion of the secondary absorbent member.

In a cross configuration assembly process, a first primary absorbent pad may be overlaid with a second primary absorbent pad in a crossing configuration, wherein first and second end regions of the first and second primary absorbent pads do not overlap each other. A secondary absorbent member may be positioned on a central region of the first primary absorbent pad. A first portion of the secondary absorbent member may then be inserted through central regions of the first primary absorbent pad and the second primary absorbent pad. In turn, the first portion of the secondary absorbent member extends outward from the second primary absorbent pad, and a second portion of the secondary absorbent member extends outward from the first primary absorbent pad. The first and second primary absorbent pads are then compressed into a generally cylindrically shaped primary absorbent member that envelops the second portion of the secondary absorbent member. A withdrawal cord is then connected with the primary absorbent member, wherein the withdrawal cord may also be inserted through the first primary absorbent pad, the second primary absorbent pad, and the secondary absorbent member.

It is to be appreciated that the systems and methods disclosed herein are applicable to work with various types of converting processes and/or machines adapted to manufacture tampons. For the purposes of a specific illustration, FIG. 1 shows an example of a tampon 100 that may be assembled in accordance with the methods and apparatuses disclosed herein. As shown in FIG. 1, the tampon 100 may include a primary absorbent member 102, a flexible member 103, and a withdrawal cord 106. The primary absorbent member 102 of the tampon 100 includes a withdrawal end 108 and an insertion end 110. As discussed below, the primary absorbent member 102 can be compressed into a generally cylindrical configuration in the radial direction, the axial direction, or in both the radial and axial directions. While the primary absorbent member 102 may be compressed into a substantially cylindrical configuration as shown for example in FIG. 1, other shapes are also possible. Such shapes may include shapes having a cross section that may be described as oval, rectangular, triangular, trapezoidal, semi-circular, hourglass, serpentine, or other suitable shapes.

It is to be appreciated that prior to compression, the primary absorbent member 102 may be formed from one or more primary absorbent pads in various shapes and sizes and may be formed with various materials and structures. The primary absorbent member 102 may also be formed as a unitary member structure or a laminate structure which includes discrete layers. The primary absorbent member may include various additional structures and materials such as described for example in U.S. Pat. No. 6,258,075 and U.S. Patent Publication No. 2004/0019317A1, both of which are incorporated by reference herein. It is to be appreciated that the discrete layers may include different materials (or same materials if desired). For example, one layer may include primarily rayon, while another layer (or layers) may include primarily cotton. In some configurations, an outer layer may be a batt formed by a rayon material which is available from Acordis Fibers Ltd. as Galaxy rayon, while an intermediate layer may be a batt formed by a cotton material which is available from Acordis Fibers Ltd.

It is to be appreciated that the primary absorbent member 102 may be constructed from a wide variety of liquid-absorbing materials used in absorbent articles, such as rayon, cotton, and comminuted wood pulp, which may be generally referred to as airfelt. Examples of additional absorbent materials include creped cellulose wadding; melt-blown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures thereof. Absorbent materials may also comprise cotton, rayon (including tri-lobal and conventional rayon fibers, and needle punched rayon), folded tissues, and woven or nonwoven materials of synthetic and/or natural fibers. The primary absorbent member 102 may include a single material or combinations of such materials. For example, primary absorbent member 102 may include a uniform material of a unitary material of rayon or cotton, or a blended material of rayon and cotton. Additionally, superabsorbent materials, such as superabsorbent polymers or absorbent gelling materials may be incorporated into the primary absorbent member 102. In some configurations, the absorbent material of the primary absorbent member 102 may be surrounded with a liquid permeable overlap material. Such overlap materials may comprise rayon, cotton, bicomponent fibers, or other natural or synthetic fibers known in the art.

The primary absorbent member 102 may be formed of a soft absorbent material such as rayon, cotton (including either long fiber cotton or cotton linters) or other suitable natural or synthetic fibers or sheeting. The materials for primary absorbent member 102 may be either a fabric, web, or batt that is formed by any suitable process known in the art such as airlaying, carding, wetlaying, hydroentangling, and other known techniques. Rayon material may be any suitable material used in disposable absorbent articles known in the art. Cotton material may also be used in the primary absorbent member 102. Such cotton material may include, long fiber cotton, short fiber cotton, cotton linters, T-fiber cotton, card strips, and comber cotton. Cotton materials may also be a scoured and bleached cotton absorbent with a glycerin finish, a leomin finish, or other suitable finish.

It is also to be appreciated that the primary absorbent member 102 may include various sizes and thicknesses suitable for compression into a tampon having a size which facilitates insertion. In some configurations, the primary absorbent member 102 may be about 9 cm in longitudinal length and about 4.5 cm in lateral width. Additionally, the lengths and widths of the primary absorbent member 102 may be configured in various ranges to facilitate width-wise expansion of the tampon in use. It is also to be appreciated that the primary absorbent member 102 may be configured with various oval basis weights. For example, in some configurations, the overall basis weight of the primary absorbent member 102 may be from about 150 g/m2 to about 750 g/m2.

With continued reference to FIG. 1, a first portion 112 of the flexible member 103 may extend outward from the withdrawal end 108 of the primary absorbent member 102. And a second portion 114 of the flexible member 103 may be enveloped, completely enwrapped, and surrounded by the primary absorbent member 102. It is to be appreciated that the flexible member 103 may be formed in various shapes and sizes and may be formed with various materials and structures. In some configurations, the flexible member 103 may be constructed to be hydrophobic, hydrophilic, absorbent, fibrous, and may comprise capillaries and/or open cell foam structures. The flexible member 103 may be arranged in a wide variety of shapes and configurations and may be generally cylindrical, spherical, semi-spherical, disc-like, planar, rectangular, "skirt-like" in shape, or may comprise "tufts" or whips of absorbent elements. The size of the flexible member 103 may vary according to its shape. For example, the flexible member 103 may be generally cylindrical and elongated. The flexible member 103 may also be configured with a longitudinal length that is the same as, less than, or greater than the longitudinal length of the primary absorbent member 102.

In some configurations, the primary absorbent member may comprise a first fibrous material composition and the flexible member may comprise a second fibrous material composition, wherein the first fibrous material composition is different from the second fibrous material composition. For example, the first fibrous material composition may be selected from the group consisting of: cotton, rayon, and combinations thereof, and the second fibrous material composition may comprise spun synthetic fibers comprising polypropylene. In some configurations, the flexible member may comprise either carded fibers or tow fibers.

In some configurations, the material used to form the flexible member 103 may be tinted or pigmented in a color that visibly contrasts with the one or more colors of the materials forming the primary absorbent member 102 and/or the withdrawal cord 106. Such a color contrast may provide a visual suggestion to a user that a differing material is present in the flexible member 103, which in turn, may suggest a functionality distinct from that of the withdrawal cord 106. In connection with appropriate information on, or associated with, packaging for the tampon product, such tinting or pigmenting may provide a reminder to the user that the flexible member 103 is present and/or may provide supplemental protection against leakage.

The flexible member 103 may be configured as a secondary absorbent member 104 that may be constructed from any of the materials described above for suitable as use in the primary absorbent member 102, such as rayon and cotton for example. In some configurations, the same materials are used in the construction of the secondary absorbent member 104 as are used in the primary absorbent member 102. The secondary absorbent member 104 may also include a suitable nonwoven structure, such as described above. In some configurations, the secondary absorbent member 104 is hydrophilic. In some embodiments, the secondary absorbent material 104 may have an advancing contact angle greater than the advancing contact angle of the primary absorbent member 102 and/or the withdrawal cord 106 (or other withdrawal mechanism), such that fluid is preferentially directed toward and absorbed by the primary absorbent member 102. In some configurations, the secondary absorbent member 104 may be treated to make it less absorbent than the primary absorbent member 102. The secondary absorbent member 104 may include various materials such, as described for example in U.S. Pat. No. 6,258,075 and U.S. Patent Publication No. 2004/0019317A1, both of which are incorporated by reference herein.

For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

In some configurations, the secondary absorbent member 104 may optionally be provided with a mechanism to preferentially direct acquired fluid toward the primary absorbent member 102. Examples of such a driving force are the use of a hydrophilicity gradient. Other mechanisms may include a density or capilarity gradient, or an osmotic driving force. The secondary absorbent member 104 may be provided with loose fiber ends to add a textured surface to the material. Capillary channel fibers may optionally be incorporated into the secondary absorbent material 104 in order to provide the driving force for acquired fluid.

In some configurations, some or all of the surrounding edges of the secondary absorbent member 104 may be fused and/or pressure bonded together. For example, fibrous materials from which the secondary absorbent member 104 may be constructed may be fused and/or bonded together, wherein such fusing and/or bonding may help reduce the appearance of loose fibrous ends and/or fraying of the secondary absorbent member 104. End edges of the secondary absorbent member 104 may be straight or curved so as to define a concave or convex shape. Examples of such edge configurations of the secondary absorbent member 104 are disclosed in U.S. Patent Application No. 62/780,388, which is incorporated by reference.

As shown if FIG. 1, the withdrawal cord 106 may be connected with the primary absorbent member 102 in various ways. As discussed in more detail below, in some configurations, the withdrawal cord 106 may be connected with and/or inserted through both the primary absorbent member 102 and the secondary absorbent member 104. The withdrawal cord 106 may be connected in various locations with the primary absorbent member 102 and/or the secondary absorbent member 104. The withdrawal cord 106 may also be positioned relative to the primary absorbent member 102 and the secondary absorbent member 104 so as to define a length having a proximal portion 116, a distal portion 118, and a central portion 120 between the proximal portion 116 and the distal portion 118. The proximal portion 116 and the central portion 120 and may be connected with the primary absorbent member 102 and/or the secondary absorbent member 104. The distal portion 118 of the withdrawal cord 106 may not be connected with the primary absorbent member 102 and the secondary absorbent member 104 and may be used to withdraw the tampon 100 after use.

It is to be appreciated that the withdrawal cord 106 may be configured in various ways and from different types of materials with various properties, such as polyester. For example, the withdrawal cord 106 may be formed from one or more continuous strings that are twisted or braided. The withdrawal cord may be configured as a ribbon, loop, tab, or the like. In some configurations, the withdrawal cord 106 may not have uniform properties throughout its length. For example, the proximal portion 116 and central portion 120 of the withdrawal cord 106 may be absorbent while the distal portion 118 may be non-absorbent. Other properties such as wicking ability, hydrophilicity, density, capillary size, width, thickness, and the like can also vary along the length of the withdrawal cord 106. In some configurations, the density of material which comprises the withdrawal cord 106 may be lower than the density of the primary absorbent member 102. In some configurations, the secondary absorbent member 104 may be more hydrophilic than the withdrawal cord 106. The withdrawal cord 106, may be made substantially hydrophobic. If the entire withdrawal cord 106 is not less hydrophilic than the secondary absorbent member 104, then at least potions of the withdrawal cord 106 (such as along the location of attachment with the secondary absorbent member 104) may be less hydrophilic than the secondary absorbent member 104.

The withdrawal cord 106 may be configured to be absorbent at locations along the central portion 120 and proximal portion 116, whereas the withdrawal cord 106 may be configured to be non-absorbent along the distal portion 118. Herein, the term "non-absorbent" refers to a structure that does not retain a significant portion of deposited fluid in its structure. In some configurations, the entire length of the withdrawal cord 106 may configured to non-absorbent. In some configurations, the materials comprising the withdrawal cord 106 may be inherently non-wettable or hydrophobic or may be treated to provide such properties. For example, a coating of wax may be applied to the withdrawal cord 106 to decrease or eliminate absorbency. The withdrawal cord 106 does not necessarily need to be non-wicking, even if a non-absorbent withdrawal cord is desired. For example, it can be desirable to provide a withdrawal cord 106 in which at least the distal portion 118 of the withdrawal cord 106 has a tendency to wick deposited fluid upwardly toward the primary absorbent member 102 and into the structure thereof.

The withdrawal cord 106 may be provided with a wicking mechanism to preferentially direct or wick acquired fluid toward the primary absorbent member 102. One example of such a driving force is produced by a hydrophilicity gradient. Other examples of the wicking mechanisms include a density gradient, a capillary gradient, and an osmotic driving force. Capillary channel fibers can optionally be incorporated into the withdrawal cord 106 in order to provide the driving force for acquired fluid described herein. An example wicking mechanism which preferentially directs acquired fluid toward the body of the primary absorbent member 102 is disclosed in the PCT Patent Publication No. WO 00/61052.

As previously mentioned, various methods herein may be utilized to assemble various configurations of tampons 100. For example, FIGS. 2-15 show views of tampon components in various stages of assembly and illustrate various method steps that may be used to assemble tampons 100 with a secondary absorbent member 104 and a primary absorbent member 102. For example, FIGS. 2-9A illustrate various methods of assembling tampons 100 with a secondary absorbent member 104, wherein the primary absorbent member 102 may be constructed from at least one primary absorbent pad 122 in a "rolled" configuration. And FIGS. 10-15 illustrate various methods of assembling tampons 100 with a secondary absorbent member 104, wherein the primary absorbent member 102 may be constructed from primary absorbent pads 122 in a "crossing" configuration.

As shown in FIGS. 2 and 3, a primary absorbent pad 122 is provided, wherein the primary absorbent pad 122 includes a first surface 124 and an opposing second surface 126. The primary absorbent pad 122 includes a first side edge 128 and a second side edge 130 separated from the first side edge 128 to define a width, W1. The primary absorbent pad 122 also includes a first end edge 132 and a second end edge 134 separated from the first end edge 132 to define a length, L1. Along the length, L1, the primary absorbent pad 122 also includes a first end region 136 and a second end region 138 separated from the first end region 136 by a central region 140.

With continued reference to FIGS. 2 and 3, a flexible member 103 that may be in the form of a secondary absorbent member 104 may be provided. The periphery of the secondary absorbent member 104 may be defined by a first end edge 142 and an opposing second end edge 144 separated by and connected with a first longitudinal side edge 146 and a second longitudinal side edge 148. The secondary absorbent member 104 may also comprise a first surface 150 and an opposing second surface 152 extending between the first end edge 142 and the second end edge 144 and extending between the first longitudinal side edge 146 and the second longitudinal side edge 148.

It is to be appreciated that the secondary absorbent member 104 may be provided in various shapes and sizes relative to the primary absorbent pad 122. For example, as shown in FIG. 3, the secondary absorbent member 104 may define a length L2 extending between the first end edge 142 and the second end edge 144 and may define a width W2 extending between the first longitudinal side edge 146 and the second longitudinal side edge 148, wherein the length L2 may be greater than the width W2. In addition, the length L1 of the primary absorbent pad 122 may be greater than the length L2 and the width W2 of the secondary absorbent member 104. In some configurations, the length L2 of the secondary absorbent member 104 may be greater than, less than, or equal to the width W1 of the primary absorbent pad 122.

During the assembly process, the secondary absorbent member 104 may be positioned on the first end region 136, the second end region 138, or the central region 140 of the primary absorbent pad 122. As such, the second surface 152 of the secondary absorbent member 104 may be positioned in direct contact with and in a facing relationship with the first surface 124 of the primary absorbent pad 122. As shown in FIG. 3, the secondary absorbent member 104 may be positioned such that the entire width W2 of the secondary absorbent member 104 extends along a portion of the length L1 of the primary absorbent pad 122, and the length L2 of the secondary absorbent member 104 extends partially along the width W1 of the primary absorbent pad 122. As such, the secondary absorbent member 104 is positioned on the primary absorbent pad 122 such that a first portion 112 of the secondary absorbent member 104 extends outward from the first side edge 128 of the primary absorbent pad 122, and a second portion 114 of the secondary absorbent member 104 extends from the first side edge 128 toward the second side edge 130 of the primary absorbent pad 122.

Figure 4:
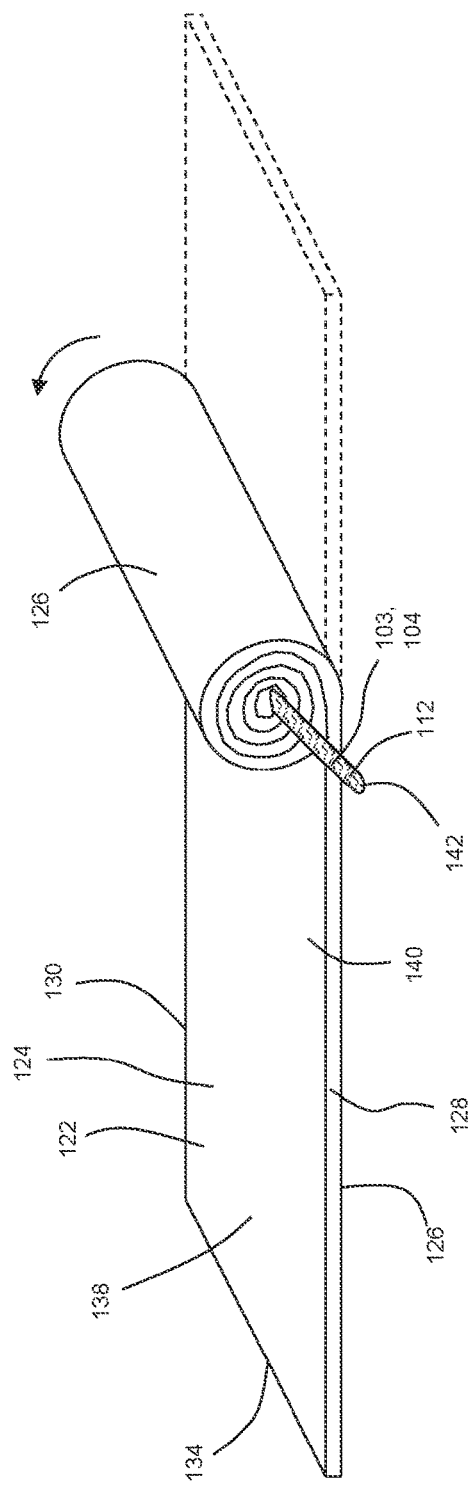
FIG. 4 is an isometric view of the primary absorbent pad of FIG. 3 being rolled from an end region into a cylindrically shaped primary absorbent member.
Figure 5:
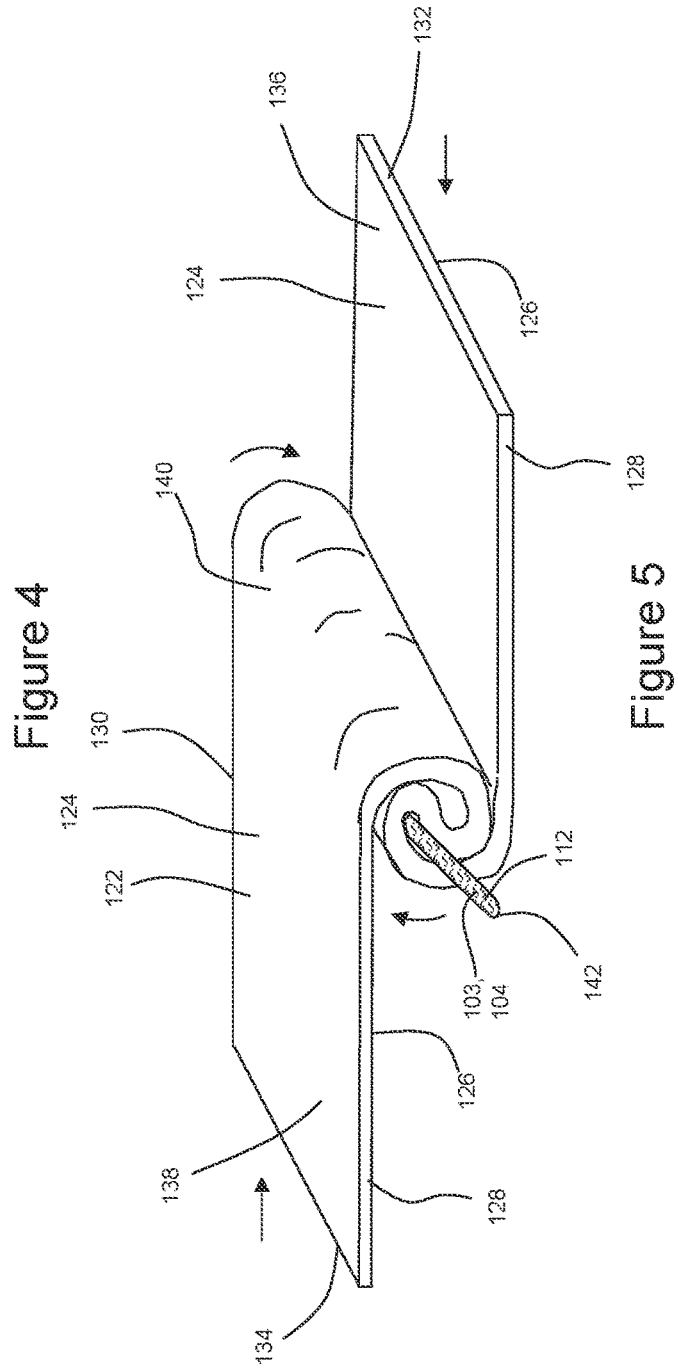
FIG. 5 is an isometric view of a primary absorbent pad being rolled from a central region into a cylindrically shaped primary absorbent member.

Referring now to FIGS. 3, 4, and 6, the primary absorbent pad 122 may be rolled into a generally cylindrically shaped primary absorbent member 102 having an insertion end 110 and a withdrawal end 108. As such, the first side edge 128 of the rolled primary absorbent pad 122 may define the withdrawal end 108 of the primary absorbent member 102, and the second side edge 130 of the rolled primary absorbent pad 122 may define the insertion end 110 of the primary absorbent member 102. As shown in FIG. 6, the primary absorbent member 102 envelops the second portion 114 of the secondary absorbent member 104. More particularly, the first portion 112 of the secondary absorbent member 104 extends outward from the withdrawal end 108 of the primary absorbent member 102, and the second portion 114 of the secondary absorbent member 104 is enveloped by the rolled primary absorbent pad 122. Depending on the relative sizes and placements of the secondary absorbent member 104 and the primary absorbent pad 122, the second end edge 144 of the secondary absorbent member 104 may also be enveloped by the primary absorbent member 102. In some configurations, the second end edge 144 of the secondary absorbent member 104 may extend to the insertion end 110 of the primary absorbent member 102 and may not be enveloped thereby. It is to be appreciated that the primary absorbent pad 122 is formed into the primary absorbent member 102 of the tampon 100, and thus, may be constructed from the same materials and/or may include the same fluid handling properties as the primary absorbent member 102 described above. It is also to be appreciated that the primary absorbent pads 122 discussed herein may be formed as a single layer substrate or may be formed as a laminate of two or more substrate layers.

It is to be appreciated that the primary absorbent pad 122 may be rolled in various ways to form the primary absorbent member 102. It is also to be appreciated that the secondary absorbent member 104 may be placed in various positions relative to the length L1 of the primary absorbent member 102 prior to rolling the primary absorbent pad 122. For example, as shown in FIGS. 3 and 4, the secondary absorbent member 104 may be positioned adjacent the first end edge 132 of the primary absorbent pad 122 prior to rolling. The primary absorbent pad 122 may then be rolled onto itself beginning at the first end edge 132 and ending with the second end edge 134. Thus, the first edge 132 may be located in a radially inward position of the primary absorbent member 102, and the second edge 134 may be located in a radially outward position of the primary absorbent member 102.

In some configurations, the secondary absorbent member 104 may be positioned in the central region 140 of the primary absorbent pad 122 prior to rolling. The primary absorbent pad 122 may also be rolled onto itself beginning in the central region 140. Thus, the first end edge 132 and the second end edge 134 may be located in a radially outward position of the primary absorbent member 102 relative to the central region 140 of the rolled primary absorbent pad 122 and/or radially outward relative to the secondary absorbent member 104.

As discussed above, the tampons 100 herein may include a withdrawal cord 106 connected with the primary absorbent member 102. As shown in FIG. 6, during the tampon assembly process, the withdrawal cord 106 may be inserted through the primary absorbent pad 122 in the rolled configuration. The withdrawal cord 106 may also be inserted through the second portion 114 of the secondary absorbent member 104 that is enveloped by the primary absorbent member 102. As such, the withdrawal cord 106 may be used to connect the primary absorbent pad 122 and the secondary absorbent member 104 together. The withdrawal cord 106 may also be tied to itself in various ways and in various locations.

It is to be appreciated that the withdrawal cord 106 may also be connected with the primary absorbent pad 122 before or during the primary absorbent pad rolling process in various ways along with the secondary absorbent member 104. For example, as shown in FIGS. 7A and 7B, the withdrawal cord 106, the secondary absorbent member 104, and the primary absorbent pad 122 may be sewn together with one or more threads 154. It is also to be appreciated that the withdrawal cord 106 and the secondary absorbent member 104 may be sewn to the primary absorbent pad 122 in the same location or in separate locations on the primary absorbent pad 122 prior to rolling the primary absorbent pad 122. In some configurations, the withdrawal cord 106 may extend along the first surface 150 of the second portion 114 of the secondary absorbent member 104 and the first surface 124 of the primary absorbent pad 122. In some configurations, the withdrawal cord 106 may be positioned between the second surface 152 of the secondary absorbent member 104 and the first surface 124 of the primary absorbent pad 122 prior being sewn together with the primary absorbent pad 122. Various manners of stitching may be used, such as disclosed for example disclosed in U.S. Pat. No. 6,887,226, which is incorporated by reference. In some configurations, the withdrawal cord 106 may be stitched with the thread 154 according to the stitching manner called "Double Ring Stitching" which is described in the Japanese Industrial Standards (JIS) No. B 9070.

In some configurations, the withdrawal cord 106 may be connected with the primary absorbent member 102 by looping the withdrawal cord 106 around the primary absorbent pad 122. For example, as shown in FIGS. 8A and 8B, the withdrawal cord 106 may be looped around the first side edge 128 and the second side edge of the primary absorbent pad before rolling the primary absorbent pad 122 to form the primary absorbent member 102. It is to be appreciated that the looped withdrawal cord 106 and the secondary absorbent member 104 may be positioned together or in separate locations along the length of the primary absorbent pad 122.

In some configurations, the secondary absorbent member 104 may be made from material that is integrated with the withdrawal cord material during construction of the withdrawal cord 106 and secondary absorbent member 104 by advancing both materials through a tubular weaver. As such, the withdrawal cord 106 may include intermittent lengths of interwoven secondary absorbent material, such as disclose for example in U.S. Pat. No. 6,258,074 and U.S. Patent Publication No. U.S. 2004/0019317A1. Thus, as shown in FIGS. 9A and 9B, the withdrawal cord 106 and integrated secondary absorbent member 104 may be connected with the primary absorbent pad 122 prior to the rolling process. In some examples, the withdrawal cord 106 and integrated secondary absorbent member 104 may be connected with the primary absorbent pad 122 by looping around the first side edge 128 and the second side edge 130 of the primary absorbent pad 122. In addition to or instead of looping, the withdrawal cord 106 and integrated secondary absorbent member 104 may be sewn to the primary absorbent pad 122.

In some configurations, the primary absorbent pad 122 may also be rolled onto itself in such a way that the secondary absorbent member 102 is not also rolled onto itself, but rather is enveloped between neighboring layers of the rolled primary absorbent pad 122. During the rolling process, the entirety of outer periphery of the first portion 112 of the secondary absorbent member 104 defined by first surface 150 and second surface 152 between the first side edge 146 and second side edge 148 may be in direct contact with and in facing relationship with the first surface 124 and/or second surface 126 of the primary absorbent pad 122. In some configurations, the secondary absorbent member 104 may be folded or wrapped around the withdrawal cord 106 while the primary absorbent pad 122 is rolled such that the secondary absorbent member 104 fully envelops a discrete length of the withdrawal cord 106.

As mentioned above, tampons 100 according to the present disclosure may also be constructed with a secondary absorbent member 104 and a primary absorbent member 102 constructed from primary absorbent pads 122 in a crossing configuration.

For example, as shown in FIG. 10, a first primary absorbent pad 122a and a second primary absorbent pad 122b may be provided. The first primary absorbent pad 122a and the second primary absorbent pad 122b may include the features described above with reference to the primary absorbent pad 122 in FIGS. 2 and 3. As such, the first primary absorbent pad 122a and the second primary absorbent pad 122b of FIG. 10 may each include a first surface 124 and an opposing second surface 126. The first primary absorbent pad also includes a first end region 136 and a second end region 138 separated from the first end region 136 by a central region 140. Similarly, the second primary absorbent pad 122b also includes a first end region 136 and a second end region 138 separated from the first end region 136 by a central region 140. During the assembly process, the first primary absorbent pad 122a and/or the second primary absorbent pad 122b may be placed such that the second surface 126 of the first primary absorbent pad 122a is positioned in direct contact with and in facing relationship with the first surface 124 of the second primary absorbent pad 122b. As shown in FIGS. 10 and 11, the central region 140 of the first primary absorbent pad 122a may overlay the central region 140 of the second primary absorbent pad 122b in a crossing configuration, wherein the first end regions 136 and the second end regions 138 of the first primary absorbent pad 122a and second primary absorbent pad 122b do not overlap each other.

As shown in FIG. 11, apertures 156 may be formed in the central region 140 of the first primary absorbent pad 122a and the central region 140 of the second primary absorbent pad 122b. The apertures 156 may be formed while first and second primary absorbent pads 122a, 122b are in the overlapping configuration, and thus may be aligned to define a continuous aperture 156 extending through both the first primary absorbent pad 122a and the second primary absorbent pad 122b.

As shown in FIGS. 11 and 12, a secondary absorbent member 104 may be provided. The secondary absorbent member 104 may also include a first surface 150 and an opposing second surface 152. It is to be appreciated that the secondary absorbent member 104 may be provided in various shapes and sizes. During the assembly process, the secondary absorbent member may be placed on the central region 140 of the first primary absorbent pad 122a. As such, the second surface 152 of the secondary absorbent member 104 may be positioned in direct contact with and in a facing relationship with the first surface 124 of the first primary absorbent pad 122a such that the aperture 156 is covered by the secondary absorbent member 104.

Referring now to FIGS. 12 and 13, a first portion 112 of the secondary absorbent member 104 may be inserted through the aperture 156 extending through the central regions 140 of the first primary absorbent pad 122a and the second primary absorbent pad 122b. As such, the first portion 112 of the secondary absorbent member 104 may extend outward from second surface 126 of the second primary absorbent pad 122b, and a second portion 114 of the secondary absorbent member 104 may extend outward from the first surface 124 of the first primary absorbent pad 122a. It is to be appreciated the secondary absorbent member 104 may be configured in various shapes and sizes. For example, as shown in FIG. 11, the secondary absorbent member 104 may be circular shaped, and as such, may define an outer circumferential region 151 surrounding an inner radial region 153. In turn, the central region may comprise the first portion 112 of the secondary absorbent member 104. In turn, the inner radial region 153 may comprise the first portion 112 of the secondary absorbent member 104, and the outer circumferential region 151 may comprise the second portion 114. In another example, the secondary absorbent member 104 may be rectangular or square shaped, and as such, may comprise a first end region and a second end region separated from the first end region by a central region.

It is to be appreciated that the first portion 112 of the secondary absorbent member 104 may be inserted through the central regions 140 of the first and second primary absorbent pads 122a, 122b in various ways. For example, an insertion tool 158 such as shown in FIG. 12 may be used to force the first portion 112 of the secondary absorbent member 104 through the first and second primary absorbent members 122a, 122b. The tool 158 may include an insertion end region 160 connected with an extending from a base end region 162. The insertion end region 160 may define a perimeter that is smaller than a perimeter of the base end region 162. As such, the insertion end region 160 may be sized such that the insertion end region 160 and the first portion 112 of the secondary absorbent member 104 can be forced through the apertures 156 in the first and second primary absorbent members 122, 122b, whereas the base end region 158 may be too large to pass through the aperture 158.

It is to be appreciated that some assembly operations may not include a step of creating an aperture 156 extending through the first and second primary absorbent pads 122a, 122b prior to inserting the secondary absorbent member 104 therethrough. For example, in some configurations, the first portion 112 of the secondary absorbent member 104 may be forced through the first and second primary absorbent pads 122a, 122b while simultaneously piercing the central regions 140 of the first and second primary absorbent pads 122a, 122b, such as with a punch press type operation.

Figure 15:
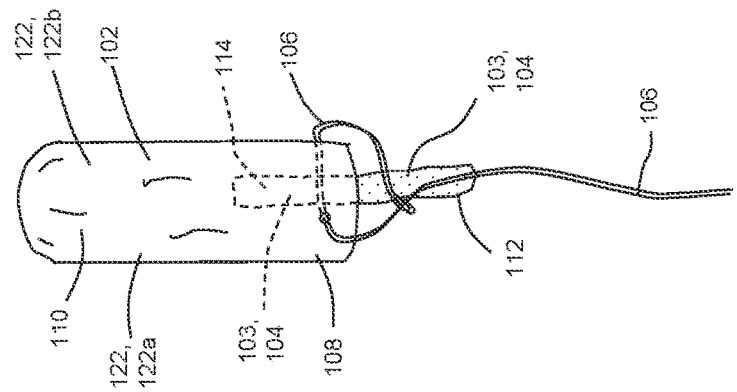
FIG. 15 is an isometric view of a withdrawal cord inserted through a primary absorbent member constructed from the compressed primary absorbent pads and secondary absorbent member of FIG. 14.
Figure 14:
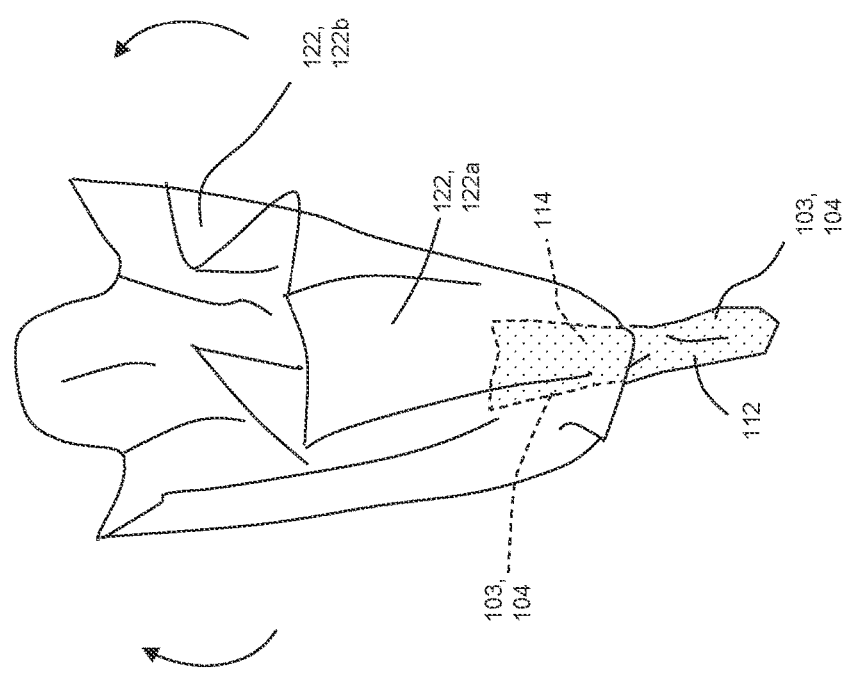
FIG. 14 is an isometric view of the first primary absorbent pad and the second primary absorbent pad being compressed into a cylindrically shaped primary absorbent member.

After the first portion 112 of the secondary absorbent member 104 is inserted through the first and second primary absorbent pads 122a, 122b, the first primary absorbent pad 122a and the second primary absorbent pad 122b may be formed and compressed into a generally cylindrically shaped primary absorbent member 102, such as shown in FIGS. 14 and 15. During the forming operation, the first and second primary absorbent pads 122a, 122b may be formed to completely envelope the second portion 114 of the secondary absorbent member 104. In turn, the primary absorbent member 102 envelops the second portion 114 of the secondary absorbent member 104. It is to be appreciated that the first and second primary absorbent pads 122a, 112b may be combined to form the primary absorbent member 102, and thus, may be constructed from the same materials and/or may include the same fluid handling properties as the primary absorbent member 102 described above. It is also to be appreciated that the first and second primary absorbent pads 122a, 122b discussed herein may be formed as a single layer substrate or may be formed as a laminate of two or more substrate layers.

A withdrawal cord 106 may also be connected with the primary absorbent member. For example, as shown in FIG. 15, the withdrawal cord 106 may be inserted through the primary absorbent member 102 and tied to itself. As such, the withdrawal cord 106 may extend through the first primary absorbent pad 122a and the second primary absorbent pad 122b. The withdrawal cord 106 may also be inserted through the second portion 114 of the secondary absorbent member 104 that is enveloped by the primary absorbent member 102. As such, the withdrawal cord 106 may be used to connect the first primary absorbent pad 122a, the second absorbent pad 122b, and the secondary absorbent member 104 together.

It is to be appreciated that the assembly processes herein may be configured in various ways to assemble tampons 100 with various component configurations. For example, the primary absorbent member 102 may be surrounded with a liquid permeable overwrap material. Such overwrap materials may comprise rayon, cotton, bicomponent fibers, or other suitable natural or synthetic fibers known in the art. As such, the assembly process may be configured to apply the overwrap material to the primary absorbent member 102 before being combined with the secondary absorbent member 104. In some configurations, the assembly process may be configured to apply the overwrap material to the primary absorbent member 102 and possibly the secondary absorbent member 104 after the primary absorbent member 102 and the secondary absorbent member 104 are combined.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making a tampon, the method comprising steps of:
   providing a first primary absorbent pad comprising a first end region and a second end region separated from the first end region by a central region;
   providing a second primary absorbent pad comprising a first end region and a second end region separated from the first end region by a central region;
   overlaying the central region of the first primary absorbent pad on the central region of the second primary absorbent pad in a crossing configuration, wherein the first and second end regions of the first and second primary absorbent pads do not overlap each other;
   positioning a flexible member on the central region of the first primary absorbent pad;
   forcing a first portion of the flexible member through the central region of the first primary absorbent pad and the central region of the second primary absorbent pad, wherein the first portion of the flexible member extends outward from the second primary absorbent pad and a second portion of the flexible member extends outward from the first primary absorbent pad;
   compressing the first primary absorbent pad and the second primary absorbent pad into a generally cylindrically shaped primary absorbent member that envelops the second portion of the flexible member; and
   connecting a withdrawal cord with at least one of the first primary absorbent pad and the second primary absorbent pad.

2. The method of claim 1, wherein the flexible member comprises a secondary absorbent member.

3. The method of claim 1, wherein connecting the withdrawal cord further comprises inserting the withdrawal cord through the first primary absorbent pad, the second primary absorbent pad, and the flexible member.

4. The method of claim 1, comprising forming apertures in the central regions of the first primary absorbent pad and the second primary absorbent pad.

5. The method of claim 4, wherein forcing the first portion of the flexible member further comprises inserting the first portion of the flexible member through the apertures.

6. The method of claim 4, wherein forming apertures further comprises punch pressing the first portion of the flexible member through the first and second primary absorbent pads.

7. The method of claim 1, wherein the flexible member comprises a first end region and a second end region separated from the first region by a central region, and wherein the central region comprises the first portion of the flexible member.

8. The method of claim 1, wherein the flexible member comprises an outer circumferential region surrounding an inner radial region, wherein the inner radial region comprises the first portion of the flexible member and wherein the outer circumferential region comprises the second portion.

9. A method for making a tampon, the method comprising steps of:
   providing a first primary absorbent pad comprising a first end region and a second end region separated from the first end region by a central region;
   providing a second primary absorbent pad comprising a first end region and a second end region separated from the first end region by a central region;
   overlaying the central region of the first primary absorbent pad on the central region of the second primary absorbent pad in a crossing configuration, wherein the first and second end regions of the first and second primary absorbent pads do not overlap each other;
   positioning a flexible member on the central region of the first primary absorbent pad, wherein the flexible member comprises a secondary absorbent member;
   forcing a first portion of the flexible member through the central region of the first primary absorbent pad and the central region of the second primary absorbent pad, wherein the first portion of the flexible member extends outward from the second primary absorbent pad and a second portion of the secondary absorbent member extends outward from the first primary absorbent pad; and
   compressing the first primary absorbent pad and the second primary absorbent pad into a generally cylindrically shaped primary absorbent member that envelops at least a portion of the second portion of the flexible member.

10. The method of claim 9, comprising connecting a withdrawal cord with the primary absorbent member.

11. The method of claim 9, comprising forming apertures in the central regions of the first primary absorbent pad and the second primary absorbent pad.

12. The method of claim 11, wherein forcing the first portion of the secondary absorbent member further comprises inserting the first portion of the flexible member through the apertures.

13. The method of claim 11, wherein forming apertures further comprises punch pressing the first portion of the secondary absorbent member through the first and second primary absorbent pads.

14. A method for making a tampon, the method comprising steps of:
   providing a first primary absorbent pad comprising a first end region and a second end region separated from the first end region by a central region;
   providing a second primary absorbent pad comprising a first end region and a second end region separated from the first end region by a central region;
   overlaying the central region of the first primary absorbent pad on the central region of the second primary absorbent pad in an overlapping configuration, wherein at least a portion of the first and second end regions of the first and second primary absorbent pads do not overlap each other;
   positioning a flexible member on the central region of the first primary absorbent pad;
   forcing a first portion of the flexible member through the central region of the first primary absorbent pad and the central region of the second primary absorbent pad, wherein the first portion of the flexible member extends outward from the second primary absorbent pad and a second portion of the flexible member extends outward from the first primary absorbent pad;

compressing the first primary absorbent pad and the second primary absorbent pad into a generally cylindrically shaped primary absorbent member that envelops the second portion of the flexible member; and wherein the flexible member comprises a secondary absorbent member.

15. The method of claim 14, comprising connecting a withdrawal cord with at least one of the first primary absorbent pad and the second primary absorbent pad.

16. The method of claim 15, wherein at least a portion of the withdrawal cord is less hydrophilic than the second primary absorbent pad.

17. The method of claim 15, wherein the withdrawal cord comprises a proximal portion, a distal portion, and a central portion between the proximal portion and the distal portion, and wherein at least one of the proximal portion and the central portion of the withdrawal cord is absorbent and the distal portion is non-absorbent.

18. The method of claim 14, comprising forming apertures in the central regions of at least one of the first primary absorbent pad and the second primary absorbent pad.

* * * * *